(12) United States Patent
Prochiantz et al.

(10) Patent No.: US 9,950,033 B2
(45) Date of Patent: Apr. 24, 2018

(54) USE OF ENGRAILED PROTEINS FOR INCREASING DOPAMINE SYNTHESIS BY DOPAMINERGIC NEURONS

(75) Inventors: Alain Prochiantz, Paris (FR); Kenneth Moya, Paris (FR); Rajiv Joshi, Massy (FR)

(73) Assignees: Centre National de la Recherche Scientifique, Paris (FR); College de France, Paris (FR)

(*) Notice: Subject to any disclaimer, the term of this patent is extended or adjusted under 35 U.S.C. 154(b) by 0 days.

(21) Appl. No.: 14/381,807

(22) PCT Filed: Feb. 29, 2012

(86) PCT No.: PCT/IB2012/050949
§ 371 (c)(1),
(2), (4) Date: Sep. 15, 2014

(87) PCT Pub. No.: WO2013/128239
PCT Pub. Date: Sep. 6, 2013

(65) Prior Publication Data
US 2015/0057231 A1 Feb. 26, 2015

(51) Int. Cl.
*A61K 38/00* (2006.01)
*A61K 38/17* (2006.01)

(52) U.S. Cl.
CPC ................ *A61K 38/1709* (2013.01)

(58) Field of Classification Search
None
See application file for complete search history.

(56) References Cited

U.S. PATENT DOCUMENTS 8,575,105 B2 * 11/2013 Prochiantz ......... A61K 38/1709
514/17.5
2011/0294739 A1 12/2011 Prochiantz et al.

FOREIGN PATENT DOCUMENTS

WO 2007/099227 A2 9/2007

OTHER PUBLICATIONS

Sonnier et al., 2007, J. Neurosci., 27(5):1063-71.*
Alvarez-Fischer et al., "Engrailed protects mouse midbrain dopaminergic neurons against mitochondrial complex I insults," Nature Neuroscience, 14: 1260-1266 (2011).
Prochiantz, "Engrailed Homeoproteins protect mesencephalic dopaminergic neurons in animal models of Parkinson disease," FEBS Journal, 278: 52 (2011) (abstract).
Simon et al., "Fate of Midbrain Dopaminergic Neurons Controlled by the Engrailed Genes," The Journal of Neuroscience, 21: 3126-3134 (2001).
Fuchs et al., "Engrailed signaling in axon guidance and neuron survival," European Journal of Neuroscience, 35: 1837-1845 (2012).
Written Opinion and International Search Report issued in corresponding International Patent Application No. PCT/IB2012/0504949 dated Nov. 22, 2012.

* cited by examiner

*Primary Examiner* — Olga N Chernyshev
(74) *Attorney, Agent, or Firm* — Morgan, Lewis & Bockius LLP

(57) ABSTRACT

The invention relates to the use of an Engrailed protein as a medicament for increasing dopamine synthesis by dopaminergic neurons, in particular in the management of conditions associated with a decrease of dopamine levels without loss of dopaminergic neurons.

9 Claims, 1 Drawing Sheet

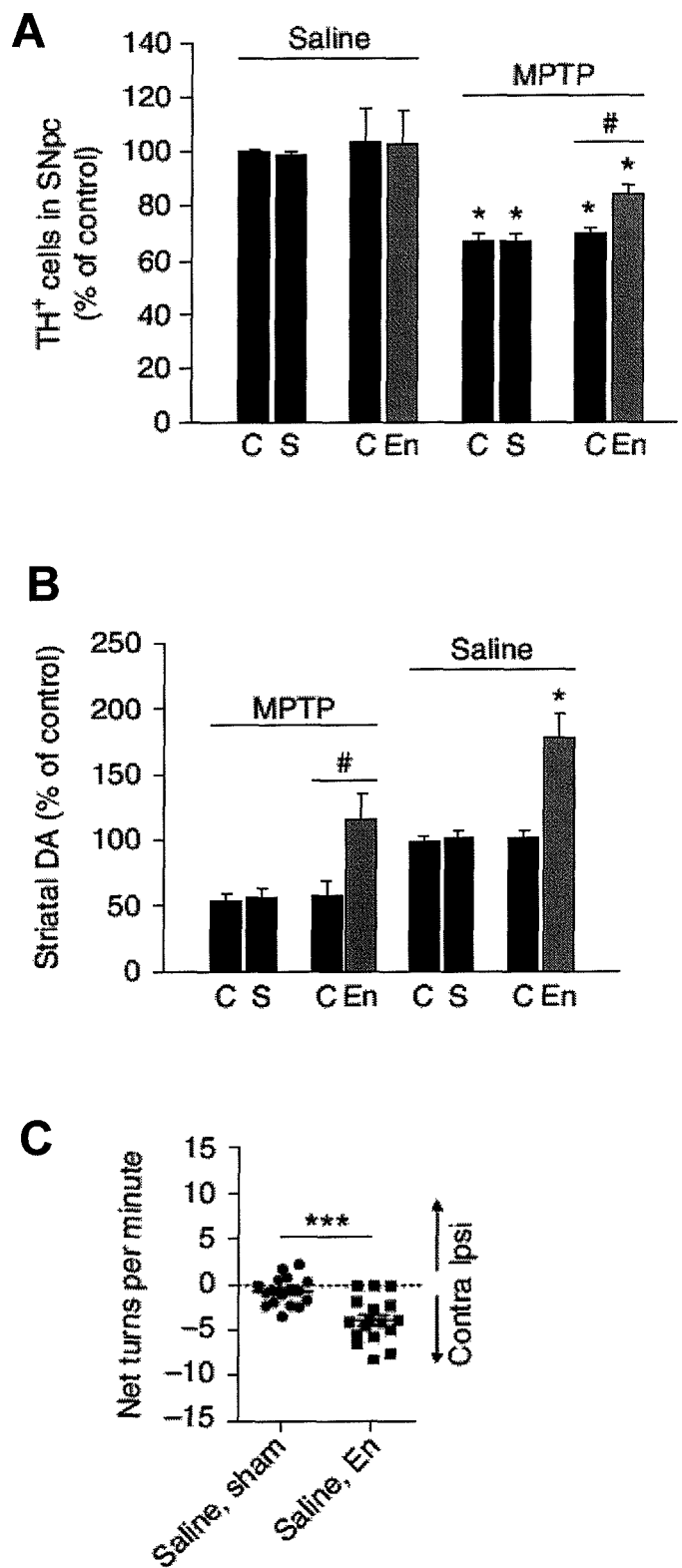

USE OF ENGRAILED PROTEINS FOR INCREASING DOPAMINE SYNTHESIS BY DOPAMINERGIC NEURONS

The present invention relates to the use of Engrailed transcription factors for increasing dopamine synthesis by dopaminergic neurons.

The Engrailed proteins are transcription factors belonging to the homeodomain protein class. Mammals possess two Engrailed genes: Engrailed-1 and Engrailed-2; the two corresponding proteins, which have similar biological activity, will be designated collectively hereafter with the general term Engrailed (EN).

In neonates and in adults, EN is expressed in the in the cerebellar granule cells and in mesencephalic dopaminergic (DA) nuclei, including the substantia nigra (SNpc which degenerate in Parkinson's disease), and the Ventral Tegmental Area (VTA).

It has been reported that EN is a survival factor for dopaminergic neurons (SIMON et al. J. Neurosci. 21 (9): 3126-34, 2001; SIMON et al., Cell Tissue Res., 318, 53-61 2004; SONNIER et al., J. Neurosci. 27, 1063-1071, 2007), and therefore it has been proposed for preventing or treating the loss of dopaminergic neurons in neurodegenerative pathologies. It has also been shown (PCT WO 2007/099227) that systemic administration of EN to mice induces an increase in the dopamine turnover in the striatum, reflected by an increase in the production of the dopamine metabolite 3,4-dihydroxyphenylacetic acid (DOPAC), without modification of dopamine levels.

The inventors have now found that besides promoting dopaminergic neuron survival in mice treated with MPTP (1-methyl-4-phenyl-1,2,3,6-tetrahydropyridine, which is a mitochondrial complex I inhibitor inducing dopaminergic neuronal death and is widely used in animal models of Parkinson disease), local administration of EN by infusion in the midbrain increases dopamine synthesis and associated motor activity, and that this effect is observed not only in MPTP-treated mice, but also in untreated mice without any loss of dopaminergic neurons.

Accordingly, the present invention relates to the use of an Engrailed protein as a medicament for increasing dopamine synthesis by dopaminergic neurons, in particular from midbrain dopaminergic neurons, and preferably in SNpc and VTA neurons.

Said medicament can be used for minimizing the decrease in dopamine synthesis associated with certain pathological or physiological conditions, and therefore it can be used for preventing or treating disorders resulting from this decrease of dopamine synthesis.

In particular it can be used in the management of conditions associated with a decrease of dopamine levels, in particular—but not only—of striatal dopamine levels, which does not result from a loss of dopaminergic neurons but from an impairment of dopamine synthesis within said neurons. Said conditions include in particular but are not limited to attention deficit hyperactivity disorder, posttraumatic stress disorder, narcolepsy, restless legs syndrome, bipolar disorder, unipolar depression and narcolepsy As indicated above, "Engrailed protein" designates here either of the proteins Engrailed-1 or Engrailed-2 of a vertebrate, as well as mixtures thereof. Preferably, said Engrailed protein(s) will be selected from the species to which the subject to be treated belongs. Said subject is preferably a mammal, and more preferably a human. Still more preferably, said subject is not suffering from a pathology associated with the loss of dopaminergic neurones.

According to the invention, said Engrailed protein is administered locally, in particular by injection or infusion into the targeted cerebral area. It can also be administered using a controlled-release device, for example an osmotic minipump implanted in the brain.

The doses of Engrailed protein to be administered in vivo in order to obtain the desired concentration in contact with the cells of the targeted brain area can be readily determined and adjusted by those skilled in the art depending, in particular, on the administration method envisaged. Typically, said Engrailed protein may be used at concentrations ranging from 0.01 to 100 µM, advantageously from 0.01 to 10 µM, and particularly advantageously from 0.01 to 0.10 µM.

The present invention will be understood more clearly by means of the further description that follows, which refers to non-limiting examples illustrating the effects of Engrailed protein on dopamine synthesis by midbrain dopaminergic neurons.

LEGEND OF FIG. 1

A) Effect of Engrailed on the number of TH+ cells in the SNpc of MPTP-injected and saline-injected mice. The non infused side of control mice injected with saline was set at 100% of TH+ cells and used for comparison with all other conditions. Data are expressed as percentage of control, n=6-10 mice per group. C, contralateral non infused side; S, sham-infused side; En, Engrailed-infused side.

B) Effect of Engrailed on the dopamine (DA) content in the striatum ipsilateral to the SNpc of MPTP-injected and saline-injected mice. C, contralateral side; S, sham-infused; En, Engrailed-infused. *$P<0.05$; # $P<0.05$; n=4-8 mice per group.

C) Effect of Engrailed on turning behaviour in saline-injected mice. Data are expressed in net turns per minute. Contra: contralateral turning; Ipsi: ipsilateral turning. ***$P<0.001$; n=17 mice per group.

EXAMPLE 1

Effect of Engrailed on Striatal Dopamine Levels in Vivo

Engrailed protects mesencephalic dopaminergic (mDA) neurons against MPTP-induced cell death. To examine the functional consequences of this Engrailed-mediated protection of mDA neurons, we measured striatal dopamine in Engrailed- or sham-infused mice injected i.p. with MPTP or saline.

Material and Methods

Mice were treated in accordance with the guide for the care and use of laboratory animals (US National Institutes of Health) and the European Directive number 86/609 (EEC Council for Animal Protection in Experimental Research and Other Scientific Utilisation). Nine-week-old male C57BL/6J mice (Janvier) were infused with Engrailed as described by SONNIER et al., (J. Neurosci. 27, 1063-1071, 2007). Briefly, En1 and En2 recombinant proteins produced in bacteria were dialyzed against 0.9% NaCl, and osmotic mini pumps (Alzet model 1002, Charles River Laboratories) were filled with 75 µg ml$^{-1}$ of each protein (4.5 µM total Engrailed) and 1.5 µg µl$^{-1}$ colominic acid in saline as vehicle. Mice were infused for 14 days into a region dorsal to the SNpc (anterior-posterior, −3.3 mm; medial-lateral, 31 mm; dorsal-ventral, −3 mm relative to bregma) according to TATTON & KISH (Neuroscience 77, 1037-1048, 1997), with a solution containing En1, En2 and colominic acid or containing only vehicle (sham-infusion), respectively.

Five days after pump implantation, mice received MPTP-HCl (Sigma-Aldrich) at a concentration of 30 mg kg−1 once a day (i.p.), or equivalent volumes of saline for 5 consecutive days ('subchronic paradigm'; SHE et al., J. Clin. Invest. 121, 930-940, 2011). For tyrosine hydroxylase-positive (TH+) cell counting and HPLC, mice were killed on day 21, 1 week after termination of Engrailed delivery.

Survival of mDA neurons was quantified by counting the number of tyrosine hydroxylase-positive neurons. Regardless of their neurotransmitter phenotype, the entire neuronal population was identified by NeuN immunofluorescence staining.

For dopamine measurements, striatal extracts were prepared and analyzed by HPLC using a reverse phase column (Nucleosil 120-3 C18; Knauer) and electrochemical detection as described by Alvarez-Fischer et al. (Exp. Neurol., 210, 182-193, 2008). Data were recorded and quantified using HPLC Chromeleon computer system (Dionex).

Results

The results are shown on FIGS. 1 A and B.

FIG. 1 A): In MPTP-injected mice, the number of TH+ cells is decreased by 32.1%±3.1% (mean±s.e.m.) on sham-infused and contralateral side (*P<0.01) when compared to saline injected-mice. The infusion of En1 and En2 reduced cell loss to 15%±3.4% (# P<0.01). In saline-injected mice, the infusion of En1 and En2 did not change the number of TH+ cells in the SNpc.

FIG. 1 B): As expected, MPTP induced a 46%±2.3% (mean±s.e.m.) decrease in striatal dopamine (DA) content in both ipsi- and contralateral sides in sham-infused, MPTP-injected mice as compared to sham-infused, saline-injected controls, reflecting mDA cell loss.

In contrast, ipsilateral striatal dopamine levels in Engrailed-infused mice injected with MPTP were higher (115.25%±19.23%) than those found in sham-infused, saline-injected controls, suggesting that Engrailed not only provided neuroprotection, but also directly enhanced dopamine synthesis. This is confirmed by the 77.5%±20.42% increase in striatal dopamine observed in saline-injected control mice infused with Engrailed when compared to baseline (sham-infused mice and the uninfused contralateral side of the same mice).

This increase in striatal dopamine in Engrailed-infused mice thus reflects not only more surviving mDA neurons (in MPTP-treated mice) but also a higher dopamine content per terminal (in MPTP- and in saline-injected mice).

EXAMPLE 2

Effect of Unilateral Engrailed Infusion on Turning Behavior

Given that Engrailed infusion into the SNpc of control mice markedly increases striatal dopamine, we tested the effect of Engrailed on turning behavior.

Amphetamine-induced rotation behavior was measured as previously described by IANCU et al., (Behav. Brain Res. 162, 1-10, 2005) in Engrailed-infused saline-injected mice versus sham-infused saline-injected mice, on day 20. Mice received 5 mg kg$^{-1}$ d-amphetamine hemisulfate salt (Sigma-Aldrich) and were placed after 20 min into individual glass bowls. Contralateral and ipsilateral turning were recorded for 5 min. Significant contralateral turning indicates an increase in nigrostriatal dopaminergic activity on the infused ipsilateral side.

The results are shown on FIG. 1 C).

Engrailed-infused mice turned preferentially contralateral to the side of infusion (−3.79±0.58 net turns per minute versus −0.65±0.37 net turns per minute for sham-infused mice; P<0.001). An uninternalized En2SR variant had no effect (data not shown), indicating that internalization of Engrailed is necessary for its protective and physiological effects.

In conclusion, the above results show that Engrailed has a physiological function in dopaminergic activity beyond neuroprotection. The increase of striatal dopamine induced by Engrailed infusion into the midbrain and the preferential turning toward the side contralateral to its infusion reflect this Engrailed-driven enhanced nigrostriatal function.

The invention claimed is:

1. A method of increasing striatal dopamine levels and promoting dopaminergic neurons survival in a subject comprising local administration of an Engrailed protein to the subject in an amount sufficient to increase striatal dopamine levels in the subject compared to striatal dopamine levels in the subject before administration of the Engrailed protein, wherein the subject presents no deficiency in Engrailed 1 and Engrailed 2 protein expression and has a decrease in dopamine synthesis, compared to a healthy subject.

2. The method of claim 1, wherein the local administration of the Engrailed protein is by injection into the brain.

3. The method of claim 1, wherein the local administration of the Engrailed protein is by injection into midbrain.

4. The method of claim 1, wherein the subject is human.

5. The method of claim 1, wherein the Engrailed protein is administered at a concentration of from about 0.01 μM to about 100 μM.

6. The method of claim 5, wherein the Engrailed protein is administered at a concentration of from about 0.01 μM to about 10 μM.

7. The method of claim 6, wherein the Engrailed protein is administered at a concentration of from about 0.01 μM to about 0.1 μM.

8. The method of claim 1, wherein the local administration of the Engrailed protein is by infusion into the brain.

9. The method of claim 1, wherein the local administration of the Engrailed protein is by infusion into midbrain.

* * * * *